United States Patent [19]

Dryden, Jr. et al.

[11] 4,057,543

[45] Nov. 8, 1977

[54] PROCESS FOR THE PREPARATION OF 17β-HYDROXY-3-OXO-17α-PREGN-4-ENE-21-CARBOXYLIC ACID γ-LACTONE

[75] Inventors: Hugh L. Dryden, Jr.; Charles S. Markos, both of Deerfield, Ill.

[73] Assignee: G. D. Searle & Co., Chicago, Ill.

[21] Appl. No.: 701,463

[22] Filed: July 1, 1976

[51] Int. Cl.$^2$ .......................... C07J 71/00; C07J 1/00
[52] U.S. Cl. .......................... 260/239.57; 260/397.1; 260/397.5
[58] Field of Search .............. 260/239.57, 397.1, 397.5

[56] References Cited
PUBLICATIONS

Jour. Med. Chem. (1963), article by Crabbe et al., pp. 182–184.

*Primary Examiner*—Elbert L. Roberts
*Attorney, Agent, or Firm*—John J. Kolano

[57] ABSTRACT

A new process utilizing certain novel intermediates for the preparation of 17β-hydroxy-3-oxo-17α-pregn-4-ene-21-carboxylic acid γ-lactone is described herein. The procedure utilizes readily available and inexpensive sarsasaponin as starting material.

4 Claims, No Drawings

PROCESS FOR THE PREPARATION OF 17β-HYDROXY-3-OXO-17α-PREGN-4-ENE-21-CARBOXYLIC ACID γ-LACTONE

Among the many steroids which have been found useful as medicines or as intermediates to other pharmacologically active substances is 17β-hydroxy-3-oxo-17α-pregn-4-ene-21-carboxylic acid γ-lactone. This compound itself possesses pharmacological activity but it can be further used to prepare other compounds such as 17β-hydroxy-3-oxo-17α-pregna-4,6-diene-21-carboxylic acid γ-lactone (as described in U.S. Pat. No. 2,900,393) a compound also known as 3-(17β-hydroxy-3-oxoandrosta-4,6-dien-17α-yl)propionic acid lactone and useful for blocking the effects of desoxycorticosterone acetate or urinary sodium and potassium. This diene can also be further reacted with thioacetic acid to give 3-(7α-acetylthio-17β-hydroxy-3-oxoandrost-4-en-17α-yl)propionic acid lactone (as described in U.S. Pat. No. 3,013,012), an anti-mineralocorticoid also known as 7α-acetylthio-17-hydroxy-3-oxo-17α-pregn-4-ene-21-carboxylic acid γ-lactone and as spironolactone.

The major source of steroidal starting materials for many years has been diosgenin, obtainable from the hydrolysis of various saponins of barbasco plant varieties of the Dioscorea family (See *J.A.C.S.*, 65, 1208 (1943) for a listing of the various species). These plant varieties are native to various regions of Mexico and the Southwest United States. However, the demand for the steroidal starting material from these plants is such that the quantities available are not sufficient to supply the large amounts of needed diosgenin starting material. Thus, alternative sources for supplying useful steroidal starting materials have been sought. The steroidal material available from other sources is not the same so that previously used procedures are usually not applicable and new synthetic procedures must be developed to take advantage of these steroidal starting materials.

The object of the present invention is to provide a useful synthetic procedure for the conversion of a readily available natural source of steroidal starting material into a steroid useful as a starting material for synthesis of a pharmacologically active compound. The present invention is thus concerned with the conversion of a steroidal material available from a natural source, i.e., sarsasaponin, (see *J.A.C.S.*, 65, 1206 (1943), into 17β-hydroxy-3-oxo-17α-pregn-4-ene-21-carboxylic acid γ-lactone. It is a further object of this invention to provide certain novel intermediates useful in the process of this invention. Sarsasaponin is a naturally occurring plant glycoside available from plant varieties such as *Radix sarsaparillae, Yucca schottii, Yucca filifera,* and *Similax ornata.*

The process of the present invention utilizes sarsasaponin as the initial starting material. Hydrolysis of that substance using a mineral acid affords sarsasapogenin which is then converted to 3β-acetoxy-5β-pregn-16-en-20-one by first contacting with acetic anhydride, N,N-dimethylformamide and lithium chloride, and then oxidizing with a solution of chromic acid in water and acetic acid. The 20-one material is converted to the corresponding oxime, which, by reaction with phosphoryl chloride and triethylamine, rearranges to give 3β-acetoxy-5β-androstan-17-one. Alkaline hydrolysis of the 3β-acetoxy compound yields the 3β-hydroxy compound which is contacted with a lower alkyl vinyl ether and a catalytic amount of acid, followed by ethynylation, to afford a 3β-[1-(lower alkoxy)ethoxy]-17α-ethynyl-5β-pregn-17β-ol. A second 1-(lower alkoxy)ethoxy group is then introduced at the 17-position in the same manner as described earlier to give the corresponding bis-[1-(lower alkoxy)ethoxy] compound. That bis-[1-(lower alkoxy)ethoxy] compound is then reacted with methylmagnesium chloride in tetrahydrofuran to give the steroid-ethynyl Grignard. The Grignard solution is then cooled and carbon dioxide is bubbled into the solution while the temperature is maintained at about −5° to 25° C. At the start of the carbon dioxide addition, the temperature of the mixture is preferably in the lower portion of the indicated temperature range. The two 1-(lower alkoxy)ethoxy groups are then removed by treating the product with a slight excess of aqueous hydrochloric acid or a similar strong acid. This reaction is preferably carried out in the presence of 2-methyl-2,4-pentanediol which readily forms a stable cyclic acetal with the acetaldehyde released during the removal of the blocking group. This avoids the occurrence of various possible side reactions with the acetaldehyde. The product obtained, 3β,17β-dihydroxy-5β-pregn-20-yne-21-carboxylic acid, is conveniently isolated as the triethylamine salt. The acid salt is then hydrogenated to give the desired propionic acid salt which is then readily lactonized by acidification. The resulting 3β,17β-dihydroxy-5β-pregnane-21-carboxylic acid γ-lactone is oxidized to the corresponding 3-one using Jones Reagent ($CrO_3$ in sulfuric acid/water). The 3-one compound is then treated with a solution of bromine in tetrahydrofuran to yield the 4-bromo-17β-hydroxy-3-oxo-5β-pregnane-21-carboxylic acid γ-lactone which, by dehydrobromination, is converted to the desired product, 17β-hydroxy-3-oxo-17α-pregn-4-ene-21-carboxylic acid γ-lactone.

The saponin hydrolysis step of the present process preferably utilizes a mineral acid such as sulfuric or hydrochloric, with a particularly preferred acid being hydrochloric acid. This reaction is most conveniently conducted in a solvent with a particularly preferred solvent being aqueous isopropanol. Other suitable solvents include the water-miscible alkanols. Time and temperature are not deemed critical to the conduct of this reaction. Time varies from 1 hour to several days, depending on the particular temperature employed.

Conversion of sarsasapogenin to the 3β-acetoxy-5β-pregn-16-en-20-one is effected by a two-step procedure involving acetylation with acetic anhydride or acetyl chloride to give the pseudosapogenin acetate, followed by oxidation of that compound with a $CrO_3$-acetic acid-water mixture. The treatment with acetic anhydride is facilitated by the addition of lithium chloride and N,N-dimethylacetamide. Time and temperature are typically in the range of 1–10 hours and room temperature to reflux. The oxidation is typically carried out at a temperature of 20°–30° C. and for a period of 1 to 6 hours.

The formation of 3β-acetoxy-5β-pregn-16-en-20-one oxime is conveniently effected in a conventional manner using hydroxylamine hydrochloride. This reaction is facilitated by the use of a basic catalyst, i.e. the addition of an organic base such as pyridine, or an inorganic base such as sodium carbonate, potassium hydroxide or sodium hydroxide. A preferred solvent for carrying out this reaction is aqueous ethanol, but other solvents such as aqueous methanol may also be used. Time and temperature are not critical, with reflux temperatures and reaction times of 2–12 hours being typical.

Rearrangement of the oxime using phosphoryl chloride and triethylamine to afford 3β-acetoxy-5β-androstan-17-one can be carried out in the presence or absence of a solvent. A particularly preferred solvent is Skellysolve C (n-heptane) but other inert organic solvents may also be used. Reaction temperatures are typically in the 0°–30° C. range and reaction temperatures vary from 1 to 10 hours.

The alkaline hydrolysis to covert the 3β-acetoxy compound to the 3β-hydroxy compound is carried out in a conventional manner. A particularly suitable base is sodium hydroxide, but others, such as potassium hydroxide, may also be used. Methanol, ethanol and other water-miscible solvents are convenient, though not absolutely necessary solvents. Reaction time is generally dependent on temperature, with higher temperatures permitting shorter reaction times.

In the lower alkyl vinyl ethers used to introduce a 1-(lower alkoxy)ethoxy group first at the 3-position and then at the 17-position, the lower alkyl group contains up to six carbon atoms. Examples of useful ethers are methyl vinyl ether, ethyl vinyl ether, butyl vinyl ether and isobutyl vinyl ether with butyl vinyl ether being particularly preferred. A preferred acid catalyst for this reaction is methanesulfonic acid, but other acids of similar strength may also be used.

The 3β-[1-(lower alkoxy)ethoxy]-compound is conveniently ethynylated at the 17-position using powdered potassium hydroxide and acetylene in a mixture of ethanol and tetrahydrofuran. Although the 17-ethynyl group is most conveniently introduced in this way, it is also possible to introduce this group by means of a Grignard reagent such as ethynylmagnesium chloride or by the corresponding lithium derivative, or by using sodium acetylide and liquid ammonia. Somewhat similarly, it is possible to use the lithium or other metal derivative of the ethynyl steroid in the carbonation process. The necessary derivatives are preferably prepared by the reaction of the ethynyl steroid with a Grignard reagent or a lithium alkyl.

The reduction of the 20-yne is conveniently effected by catalytic hydrogenation. Suitable catalysts include platinum, Raney nickel, copper-chromium oxide and palladium (optionally on a support), a particulary preferred catalyst being palladium-on-calcium carbonate. The hydrogenation is conveniently conducted in a solvent, such as any of the lower alkanols. A particularly preferred solvent is methanol with room temperature and a reaction time of about 1–5 hours also being preferred.

The lactonization of the present process is conveniently effected using a mineral acid. Suitable mineral acids include, but are not limited to, sulfuric, nitric and hydrochloric, with hydrochloric acid being particularly preferred.

The oxidation of the 3β,17β-dihydroxy-5β-pregnane-21-carboxylic acid γ-lactone to the corresponding 3-one is preferentially accomplished using Jones reagent.

The bromination at the 4-position is accomplished using a solution of bromine in an organic solvent that is inert under the reaction conditions employed. A particularly preferred solvent is tetrahydrofuran, but others such as methylene chloride, carbon tetrachloride and ethyl ether may also be used. This reaction is preferably carried out at a temperature of 0°–30° C, with 5°–10° C. being particularly preferred. Bromine is added as fast as it is decolorized and extended reaction times are avoided.

Dehydrobromination of the 4-bromo compound is accomplished using a hydrogen bromide acceptor such as magnesium oxide, lithium carbonate or tri-n-butylamine in an aprotic solvent such as N,N-dimethylformamide. Lithium chloride or lithium bromide added in a small amount facilitates the reaction. Lithium carbonate and N,N-dimethylformamide are particularly preferred. Reaction times and temperatures are not critical to the conduct of the reaction, but reflux temperatures and reaction times in the range of 4–48 hours are particularly preferrable.

The following examples describe in detail the process of the preparation of compounds of the present invention. It will be apparent to those skilled in the art that many modifications, both of materials and methods, may be practiced without departing from the purpose and intent of this disclosure. Throughout the examples hereinafter set forth, temperatures are given in degrees Centigrade (°C.) and relative amounts in parts by weight, except as otherwise noted. The relationship between parts by weight and parts by volume is the same as that existing between grams and milliliters.

EXAMPLE 1

100 Parts of crude sarsasaponin is suspended in 255 parts of ethyl acetate and heated at reflux for 0.5 hour. The mixture is filtered hot and the filter cake washed with 89 parts ethyl acetate and dried. The dried residue is mixed with 1850 parts by volume of a 15% (v/v) solution of concentrated hydrochloric acid in water and heated at 95°–101° C. for 2 hours. The hot reaction mixture is then filtered to give a precipitate which is washed with water and dried to afford crude sarsasapogenin in an 89.5% yield. This crude material is treated with 50 parts alumina and 5 parts carbon in 440 parts toluene. Filtration affords a pale yellow solution, which upon standing, yields a solid. This solid is filtered, and recrystallized from hot n-hexane to give sarsasapogenin melting at about 200°–205° C. This compound exhibits an $[\alpha]_D^{25} = -78.8° \pm 1.5$ (c=0.996% in chloroform), an $[\alpha]_{365}^{25} = -230.9° \pm 1.5$ (c=0.996% in chloroform), and is represented by the following structural formula.

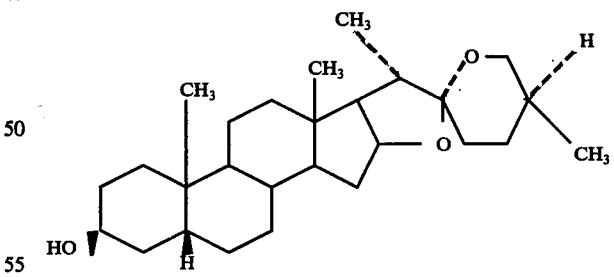

EXAMPLE 2

A mixture of 1004 parts of crude sarsasaponin, 1560 parts of isopropanol, 225 parts of water and 298 parts of concentrated hydrochloric acid is heated at reflux for 2 hours. Then, an additional 166 parts of concentrated hydrochloric acid dissolved in 400 parts of water is added and refluxing continued for a further 1.5 hour. The reaction mixture is diluted to 12,000 parts by volume with water and ice and the resulting precipitate collected, washed with water and air-dried to afford crude sarsasapogenin in an 89% yield. This crude material is dissolved in toluene with warming, treated with 190 parts of alumina, 45 parts of charcoal, and filtered hot. The toluene solution is then cooled to room temperature and refiltered. The toluene is removed in vacuo to leave a volume of about 1,000 parts. This solution is diluted with n-hexane to about 3,500 parts by volume causing the separation of a dark precipitate. The solution is filtered, treated with charcoal, warmed to about 60° C., and filtered through diatomaceous earth under vacuum. Cooling affords crystals which are separated, washed successively with 1,500 parts by volume of the mother liquors and 1,000 parts of n-hexane and dried in a steam oven. Recrystallization from a mixture of acetone and n-hexane affords sarsasapogenin, identical to the product of Example 1.

EXAMPLE 3

193 Parts of sarsasapogenin, 20.1 parts of lithium chloride, 112 parts of N,N-dimethylacetamide and 188 parts of acetic anhydride are combined and heated rapidly to reflux. After heating at about 166° C. for 90 minutes, the reaction mixture is cooled to about 80° C. 260 Parts of acetic acid and 12.5 parts of water is then added to destroy the excess acetic anhydride.

The resulting mixture is then cooled to 29° C. with an ice-water bath and a solution of 96 parts chromium trioxide in 200 parts by volume of 50:50 water-acetic acid mixture added slowly so as to maintain the temperature between 28°-32° C. After the addition is completed, the mixture is stirred at about 29° C. for 35 minutes, and 34 parts of isopropanol added. After heating to reflux at 108° C. for 2 hours, the solution is slowly diluted with water causing a gum to separate. The aqueous layer is decanted and washed twice with ether. The gum is dissolved in ether, combined with the ether extracts, washed twice with water, four times with saturated sodium bicarbonate and once with saturated sodium chloride solution. After filtering through sodium sulfate, the ether is stripped in vacuo to leave an oil. This oil is dissolved in boiling methanol, and cooled in an ice-bath to afford a crystalline product. The crystals are separated, washed with 10% aqueous methanol and air-dried to afford 3β-acetoxy-5β-pregn-16-en-20-one in 50.7% yield. This compound melts at about 144°-145° C. and exhibits a λ$_{max}$ at 238.5 mμ, ε 16,000 (Methanol) and is represented by the following structural formula

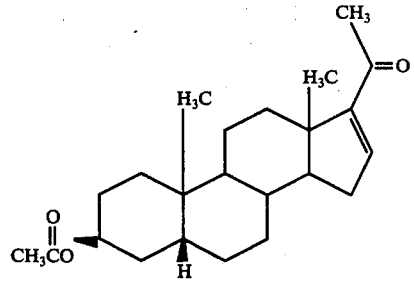

EXAMPLE 4

56 Parts of 3β-acetoxy-5β-pregn-16-en-20-one is mixed with 315 parts of ethanol and heated to reflux to effect solution. Then, 11.6 parts of hydroxylamine hydrochloride, 14.7 parts of pyridine, 11.2 parts of water and 395 parts of ethanol is added and the refluxing continued for 2 hours. Distillation is initiated and continued until the pot volume is about 200 parts. The pot residue is then chilled to afford a precipitate that is washed first with 150 parts by volume chilled distillate and then with 200 parts of water. Further cooling of the mother liquor affords a second crop. The first and second crops are combined to give 3β-acetoxy-5β-pregn-16-en-20-one oxime, in a yield of 83.4%. This compound melts at about 180°-183° C. and is represented by the following structural formula.

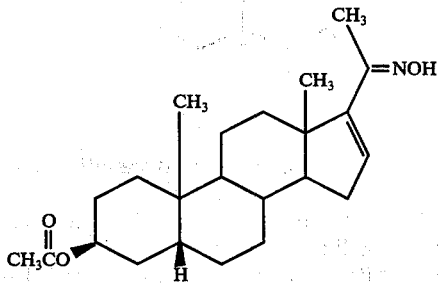

EXAMPLE 5

To a mixture of 48.6 parts of 3β-acetoxy-5β-pregn-16-en-20-one oxime, 35.3 parts of triethylamine, and 410 parts of n-heptane cooled to about 15° C. is added 30.6 parts of phosphorus oxychloride over a period of 0.5 hour while maintaining the temperature at 15°-21° C. The resulting suspension is stirred at this temperature for a further 2 hours. Then, 36 parts of water is slowly added while maintaining the temperature below 30° C. A further 120 parts water is added and the n-heptane is distilled from the biphasic mixture at about 85° C. Increasing the temperature to about 105° C. results in the precipitation of a solid product in the aqueous residue. The mixture is cooled, the precipitate collected, washed successively with water, dilute sodium bicarbonate, and again with water to afford 3β-acetoxy-5β-androstan-17-one in a yield of 98.6%. This compound melts at about 158°-159° C. and exhibits infrared absorption maxima in chloroform at 2950, 1740, 1452, 1380, 1260 and 1022 cm$^{-1}$ and is represented by the following structural formula.

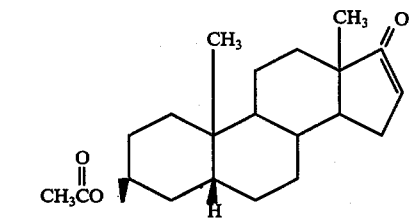

EXAMPLE 6

A solution of 7.6 parts of sodium hydroxide in 25 parts of water is added to a solution of 42.5 parts of 3β-acetoxy-5β-androstan-17-one in 140 parts of methanol with stirring. The resultant mixture is heated to reflux for 2 hours whereupon distillation is initiated and 109 parts of methanol are removed. The remaining methanol is removed by evaporation and the resulting crystalline solid is diluted with water and stirred. The crystals are collected by filtration, washed with water until the washings are about pH 6 and air-dried to afford, in 98.5% yield, 3β-hydroxy-5β-androstan-17-one. This compound melts at about 152°-155° C. and exhibits infrared absorption maxima in chloroform at 3620, 2940, 1735 cm⁻¹ and is represented by the following structural formula.

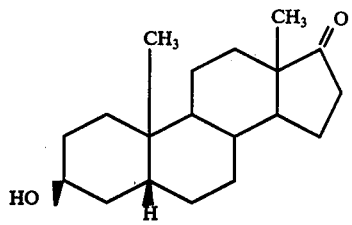

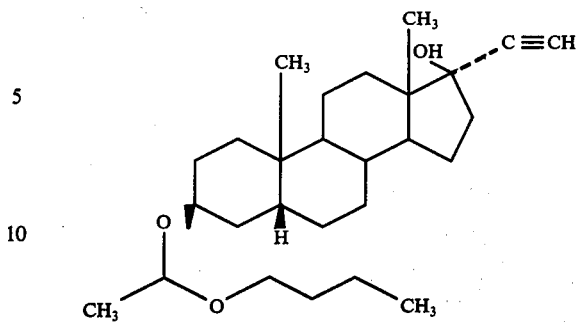

EXAMPLE 7

0.2 Parts by volume of methanesulfonic acid dissolved in 1.6 parts of tetrahydrofuran is added to 36 parts of finely ground 3β-hydroxy-5β-androstan-17-one in 15 parts of butyl vinyl ether and 32 parts of tetrahydrofuran. After 20 minutes, an additional 0.3 parts by volume of methanesulfonic acid is added and stirring continued for an additional 30 minutes. 0.6 Part of triethylamine is added to quench the excess methanesulfonic acid.

A slurry is prepared from 37.5 parts of potassium hydroxide, 7.7 parts of ethanol and 85.5 parts of tetrahydrofuran and this slurry is cooled to about −10° C. and saturated with acetylene. Then, the solution of 3β-(1-butoxyethoxy)-5β-androstan-17-one obtained in the preceding paragraph is added while the temperature is maintained at −8° to −14° C. The mixture is stirred at this temperature for 2 hours and 40 minutes, and the reaction is then quenched with 36 parts of acetic acid and 54 parts of water. Then, 26 parts of n-hexane is added and the mixture warmed to about 10° C. The aqueous and organic layers are separated and the aqueous layer extracted twice with portions of tetrahydrofuran. The tetrahydrofuran extracts and the organic layer are then combined, dried over potassium carbonate and diatomaceous earth and filtered through diatomaceous earth. The solvents are removed under reduced pressure to afford, as an oil, 3β-(1-butoxyethoxy)-17α-ethynyl-5β-androstan-17β-ol. The compound is represented by the following structural formula.

EXAMPLE 8

To a cooled solution of approximately 36 parts of 3β-(1-butoxyethoxy)-17α-ethynyl-5β-androstan-17β-ol in 47 parts of water tetrahydrofuran is added 14.8 parts of butyl vinyl ether and 1.3 part by volume of a solution of 0.2 part of methanesulfonic acid in 1.6 parts of tetrahydrofuran and the reaction is continued for 1.5 hours. Then, 42 parts of tetrahydrofuran and 1 part of triethylamine is added to quench any excess methanesulfonic acid. The resulting mixture, containing 3β,17β-bis(1-butoxyethoxy)-17α-ethynyl-5β-androstane is heated to about 50° C. and 42.5 parts by volume of a 3 M solution of methylmagnesium chloride in tetrahydrofuran is added. The mixture is heated to reflux for 1 hour and then cooled to about 7° C. Carbon dioxide is bubbled through the mixture for 30 minutes. Addition of 42.5 parts by volume of 2-methyl-2,4-pentanediol is followed by addition of a solution of 22.4 parts concentrated hydrochloric acid in 66 parts of water and the reaction mixture heated to 37°–40° C. for 0.5 hour with rapid stirring. The mixture is then cooled to room temperature and diluted with 99 parts of tetrahydrofuran. The aqueous and tetrahydrofuran layers are separated. The tetrahydrofuran layer is washed twice with 47 parts by volume of brine, once with 10 parts of water, dried over anhydrous magnesium sulfate and diatomaceous earth, and filtered through diatomaceous earth. Addition of 15.4 parts of triethylamine affords a solid precipitate which is collected, washed with tetrahydrofuran and dried. A second crop of crystals is obtained from the mother liquor by diluting with ether. The crystals are combined with the earlier crop to afford, in 75% yield, 3β,17β-dihydroxy-5β-pregn-20-yne-21-carboxylic acid triethylamine salt. This compound melts at about 182°–187° C. and is represented by the following structural formula.

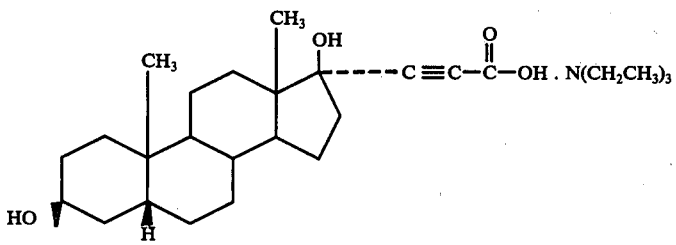

EXAMPLE 9

4.62 Parts of 3β,17β-dihydroxy-5β-pregn-20-yne-21-carboxylic acid triethylamine salt is dissolved in 120 parts of methanol. 0.46 Part of a 5% palladium-on-calcium carbonate catalyst is added and the mixture is hydrogenated at room temperature and at a pressure of 4 psi for approximately 2 hours. After removing the catalyst by filtration, the filtrate containing 3β,17β-dihydroxy-5β-pregnane-21-carboxylic acid triethylamine salt, is adjusted to pH 1 using 2.1 parts of concentrated hydrochloric acid and warmed on a steam bath to reduce the volume of the solution to about 50 parts by volume. The solution is diluted with water to give a precipitate which is filtered, washed with water and dried in vacuo to afford, in 95.7% yield, 3β,17β-dihydroxy-5β,17α-pregnane-21-carboxylic acid γ-lactone. This compound melts at about 202°–203° C., exhibits infrared absorption maxima in chloroform at 3620, 3500, 2940 and 1765 cm⁻¹ and is represented by the following structural formula.

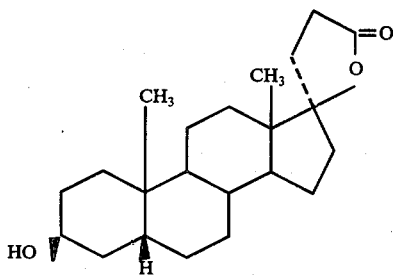

EXAMPLE 10

To a stirred solution of 26 parts of 3β,17β-dihydroxy-5β,17α-pregnane-21-carboxylic acid γ-lactone in 355 parts of acetone is added 32.5 parts by volume of Jones Reagent over a 15 minute period. When the addition is completed, the excess reagent is decomposed by the addition of isopropanol and the acetone solution decanted from the inorganic salts. The solvents are removed from the acetone solution under reduced pressure and the residue diluted with water and recombined with the inorganic salt. Cooling affords a precipitate which is filtered, washed with water and air-dried to afford 17β-hydroxy-3-oxo-5β,17α-pregnane-21-carboxylic acid γ-lactone in a 98.2% yield. This compound melts at about 165°–183° C. and represented by the following structural formula.

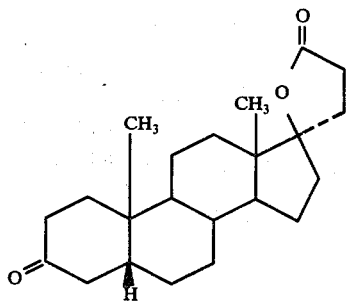

EXAMPLE 11

To a cooled solution (~5° C.) of 3.46 parts of 17β-hydroxy-3-oxo-5β,17α-pregnane-21-carboxylic acid γ-lactone in 40 parts of tetrahydrofuran is added a solution of 1.65 parts of bromine in 5.4 parts of methylene chloride over a 10 minute period while maintaining the temperature at 5°–9° C. Then, the reaction is quenched with the addition of a solution of 1.1 parts of sodium bicarbonate in 11 parts of water, followed by 50 parts of water. Removal of the organic solvents under reduced pressure affords a solid residue in the aqueous phase. The solid is collected by suction filtration and washed with water. The filter cake is stirred with 8 parts of ethanol for 0.5 hour, and cooled. The solid is then filtered, washed with 10% aqueous ethanol, and air-dried to afford, in 90% yield, 4-bromo-17β-hydroxy-3-oxo-5β,17α-pregnane-21-carboxylic acid γ-lactone. This compound exhibits infrared absorption maxima at 2950, 1770, and 1733 cm⁻¹ and is represented by the following structural formula

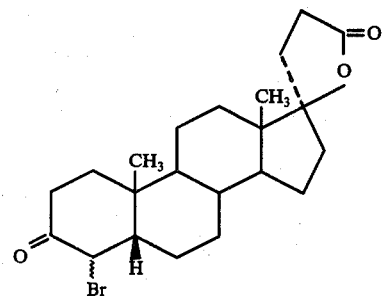

EXAMPLE 12

A mixture of 0.4 part of lithium carbonate, 0.01 part of lithium chloride and 19 parts of N,N-dimethylformamide is heated to reflux. Then, 2.1 parts of 4-bromo-17β-hydroxy-3-oxo-5β,17α-pregnane-21-carboxylic acid γ-lactone is added and the refluxing continued for 45 minutes. After cooling to 130° C., 60 parts of ice and 30 parts of water is added to afford a gum. Then, 5.9 parts of concentrated sulfuric acid is added and the mixture stirred vigorously at room temperature for 1 hour. The resulting solid is collected by suction filtration, washed with water and air-dried to afford, in 89% yield, 17β-hydroxy-3-oxo-17α-pregn-4-ene-21-carboxylic acid γ-lactone. This compound melts at about 135°–145° C. after recrystallization from aqueous methanol and is represented by the following structural formula.

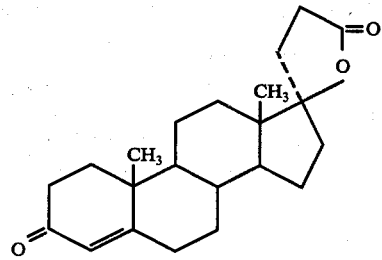

What is claimed is:

1. A process for the preparation of 17β-hydroxy-3-oxo-17α-pregn-4-ene-21-carboxylic acid γ-lactone which comprises:
   a. mineral acid hydrolysis of sarsasaponin to afford sarsasapogenin;
   b. acetylation of sarsasapogenin followed by oxidation using a mixture of chromic acid in water and acetic acid to afford 3β-acetoxy-5β-pregn-16-en-20-one;

c. conversion of the resulting 3β-acetoxy-5β-pregn-16-en-20-one to the corresponding oxime using hydroxylamine hydrochloride;

d. rearrangement of that oxime using phosphoryl chloride and triethylamine to aford 3β-acetoxy-5β-androstan-17-one;

e. alkaline hydrolysis of 3β-acetoxy-5β-androstan-17-one to afford the corresponding 3β-hydroxy compound;

f. reacting the 3-hydroxy compound with a lower alkyl vinyl ether in the presence of an acid catalyst to give a 3β-(1-lower alkoxyethoxy)-5β-androstan-17-one;

g. ethynylating the ketone by means of an ethynylating agent selected from the group consisting of potassium hydroxide and acetylene, ethynylmagnesium chloride, lithium acetylide, or sodium acetylide to give the corresponding 17α-ethynyl-17β-hydroxy compound;

h. treating this 17β-hydroxy compound with a lower alkyl vinyl ether in the presence of an acid catalyst to give the corresponding 3β,17β-bis[1-(lower alkoxy)ethoxy]-17α-ethynyl-5β-pregnane;

i. treating the resultant compound with a reagent selected from the group consisting of a Grignard reagent and lithium alkyl followed by carbonation to give 3β,17β-bis[1-(lower alkoxy)ethoxy]-5β-pregn-20-yne-21-carboxylic acid;

j. hydrolyzing the compound under mineral acid conditions to give 3β,17β-dihydroxy-5β-pregn-20-yne-21-carboxylic acid;

k. catalytic hydrogenation of this 20-yne as the triethylamine salt followed by treatment with a mineral acid to effect lactonization and give the desired 3β,17β-dihydroxy-5β,17α-pregnane-21-carboxylic acid γ-lactone;

l. oxidation of the γ-lactone to give 17β-hydroxy-3-oxo-5β,17α-pregnane-21-carboxylic acid γ-lactone;

m. treatment of the 3-oxo compound with bromine in an inert solvent to afford the corresponding 4-bromo-17β-hydroxy-3-oxo-5β,17α-pregnane-21-carboxylic acid γ-lactone;

n. dehydrobromination of the 4-bromo compound to afford 17β-hydroxy-3-oxo-17α-pregn-4-ene-21-carboxylic acid γ-lactone.

2. A process according to claim 1 for the preparation of 17β-hydroxy-3-oxo-17α-pregn-4-ene-21-carboxylic acid γ-lactone which comprises:

a. hydrochloric acid hydrolysis of sarsasaponin to afford sarsasapogenin;

b. acetylation using acetic anhydride, lithium choride and N,N-dimethylacetamide, and oxidation using a mixture of chromic acid in water and acetic acid, of sarsasapogenin to afford 3β-acetoxy-5β-pregn-16-en-20-one;

c. conversion of the resulting 3β-acetoxy-5β-pregn-16-en-20-one to the corresponding oxime using hydroxylamine hydrochloride and pyridine;

d. rearrangement of that oxime using phosphoryl chloride and triethylamine to afford 3β-acetoxy-5β-androstan-17-one;

e. alkaline hydrolysis of 3β-acetoxy-5β-androstan-17-one using sodium hydroxide to afford the corresponding 3β-hydroxy compound;

f. reacting the 3β-hydroxy compound with butyl vinyl ether in the presence of an acid catalyst to give a 3β-(1-butoxyethoxy)-5β-androstan-17 one;

g. ethynylating the ketone using potassium hydroxide and acetylene in ethanol to give the corresponding 17α-ethynyl-17β-hydroxy compound;

h. treating this 17β-hydroxy compound with butyl vinyl ether in the presence of an acid catalyst to give the corresponding 3β,17β-bis(1-butoxyethoxy)-17α-ethynyl-5β-pregnane;

i. treating the resultant compound with methylmagnesium chloride followed by carbonation to give 3β,17β-bis(1-butoxyethoxy)-5β-pregn-20-yne-21-carboxylic acid;

j. hydrolyzing the compound using hydrochloric acid to give 3β,17β-dihydroxy-5β-pregn-20-yne-21-carboxylic acid;

k. catalytic hydrogenation of the 20yne as the triethylamine salt and using a palladium-on-calcium carbonate catalyst followed by lactonization using hydrochloric acid to give the desired 3β,17β-dihydroxy-5β,17α-pregnane-21-carboxylic acid γ-lactone;

l. oxidation of the γ-lactone to give 17β-hydroxy-3-oxo-5β,17α-pregnane-21-carboxylic acid γ-lactone;

m. treatment of the 3-oxo compound with bromine in tetrahydrofuran to afford the corresponding 4-bromo-17β-hydroxy-3-oxo-5β,17α-pregnane-21-carboxylic γ-lactone; and n. dehydrobromination of the 4-bromo compound using lithium carbonate and N,N-dimethylformamide and a catalytic amount of lithium chloride to afford 17β-hydroxy-3-oxo-17α-pregn-4-ene-21-carboxylic acid γ-lactone.

3. The compound which is 3β-(1-butoxy-ethoxy)-17α-ethynyl-5β-androstan-17β-ol.

4. The compound which is 3β,17β-dihydroxy-5β-pregn-20-yne-21-carboxylic acid triethylamine salt.

* * * * *